US006473698B1

United States Patent
Albert et al.

(10) Patent No.: US 6,473,698 B1
(45) Date of Patent: Oct. 29, 2002

(54) METHOD AND APPARATUS FOR AUTOMATED ROLLING LEUKOCYTE VELOCITY MEASUREMENT IN VIVO

(75) Inventors: Thomas A. Albert, Pittsfort, NY (US); Frederick N. Miller, Louisville, KY (US)

(73) Assignee: University of Louisville Research Foundation, Inc., KY (US)

(*) Notice: Subject to any disclaimer, the term of this patent is extended or adjusted under 35 U.S.C. 154(b) by 0 days.

(21) Appl. No.: 09/553,077

(22) Filed: Apr. 20, 2000

Related U.S. Application Data
(60) Provisional application No. 60/130,626, filed on Apr. 22, 1999, and provisional application No. 60/132,579, filed on May 5, 1999.

(51) Int. Cl.⁷ .............................................. G01F 1/00
(52) U.S. Cl. .......................................... 702/45; 702/19
(58) Field of Search ........................ 382/103; 600/436; 711/147

(56) References Cited

U.S. PATENT DOCUMENTS

| | | | |
|---|---|---|---|
| 6,026,472 A | * | 2/2000 | James et al. ................. 711/147 |
| 6,175,761 B1 | * | 1/2001 | Frandsen et al. ........... 600/436 |
| 6,198,833 B1 | * | 2/2001 | Rangan et al. .............. 382/103 |

OTHER PUBLICATIONS

Taylor, J.; Chan. c., "An Intelligent Implementation Aid for Industrial Process Control Systems", Proceedings of the American Control Conference, Jun. 1999, pp 3605–3609.*

Acton, S.T.; Ley, K., "Tracking Leukocytes From In Vivo Microscopy Using Morphological Ansiotropic Diffussion", International Conference on Image Processing, 2001, Proceedings 2001, Oct. 2000, pp 300–303.*

Capson, D.W.; Maludzinski, R.A.; Feurstein, I.A., "Microcomputer–Based Interactive Tracking of Blood Cells at Biomaterial Surfaces", Biomedical Engineering, IEEE Transactions on vol. 36, Issue 8, Aug. 1989, pp 860–864.*

* cited by examiner

*Primary Examiner*—John S. Hilten
*Assistant Examiner*—Douglas N Washburn
(74) *Attorney, Agent, or Firm*—Schwegman, Lundberg, Woessner & Kluth, P.A.

(57) ABSTRACT

A time-varying image of a circulating venue containing a flow of particles is generated by imaging using a video camera and a digital frame grabber. Spatio-temporal intensity gradients within each of the images are generated. Particles are then identified within the images. A particle is matched with a corresponding identical particle from other images using, for example, a heuristic equation that measures similarity of shape, size, and position. The distance of translation of the matched particle from one image to another is determined. Leukocyte velocity is determined by dividing the translation distance by the time differential between the images. The first five statistical moments of frequency distribution of the velocity may also be determined.

12 Claims, 5 Drawing Sheets

FIG. 4A DIRECTION OF BLOOD FLOW FIG. 4B

METHOD AND APPARATUS FOR AUTOMATED ROLLING LEUKOCYTE VELOCITY MEASUREMENT IN VIVO

This application claims the benefit of priority under 35 U.S.C. §119(e) of U.S. Provisional Application Ser. No. 60/130,626, filed Apr. 22, 1999, and U.S. Provisional Patent Application Ser. No. 60/132,579, filed May 5, 1999, both of which are incorporated herein by reference in their entireties.

BACKGROUND OF THE INVENTION

1. Field of the Invention

The invention relates to real time velocity measurements of particles flowing in a venue. In one embodiment, the present invention relates to the in vivo measurement of the velocity of particles such as rolling leukocytes. The methods of the invention are also suitable for tracking the movement of larger particles or objects such as vehicles in the flow of traffic. An apparatus suited for using the method of the invention is also provided.

2. Description of the Background

It is presently impractical to implement a procedure for real time tracking of the velocity and stopping patterns of particles within a circulating venue. For purposes of describing this field and invention, by "particle" is meant a discrete object of any size from microscopic to the size of vehicles. By "venue" is meant the environment in which particles move. Circulating venues range from the size of capillaries to pipes to highways. The principles to be taught herein are applicable to any particle in any circulating venue.

Presently available technology is labor intensive, and incapable of tracking multiple venues at one time automatically and providing real time information. Such technology has application to a variety of fields, including tracking cells in the blood flow and circulation of motor vehicles in specific venues. In the latter case, the availability of such technology would permit tracking and modifying the circulation of, for example, motor vehicles during peak hours of traffic or in cases of accidents, which normally produce extended delays in circulation.

In the case of circulating cells, for example, tissue damage or infection initiates a complex chain of events in which certain substances such as cytokines and chemoattractants are released in the interstitium and diffuse towards small veins (venules). These substances activate venular endothelial cells (the cells lining the blood vessel wall) to produce and express adhesion molecules. Leukocytes in the blood then transiently attach to the endothelial cells by binding to these adhesion molecules. These attachments cause the velocity of the leukocytes to decrease relative to the plasma and red blood cells, and the leukocytes appear to "roll" along the venular wall. Additional chemo-attractants and released mediators of inflammation induce the expression of other adhesion molecules that form stronger leukocyte-endothelial interactions. The velocity of the leukocyte approaches zero as it firmly adheres or "sticks" to the vascular wall. Subsequently, these stuck leukocytes migrate through the vascular wall into the tissue where they participate in phagocytosis and the inflammatory process.

Many of the substances released by the leukocytes destroy invading bacteria and also damage host tissue. This is often a major clinical problem in inflammatory conditions. Indeed, an uncontrolled leukocyte activation may in itself be the most damaging and deleterious aspect of a disease because normal tissue may be damaged or destroyed. Continuous measurement of the velocity of leukocytes in multiple vessels during the early stages of the inflammatory response is essential to understanding and eventually controlling leukocyte function. This is also true about the continuous measurement of the velocity of other particles, such as motor vehicles, in multiple circulating venues, for understanding and modifying traffic patters. Yet, current methodology in this area is time consuming and severely limits the quantity of data that can be collected.

In vivo television microscopy may be used to view the first signs of particle behavior, e.g. in the case of leukocyte activation, which is manifested by "rolling" and then "sticking" of the leukocytes to the venular wall. To be able to quantify this early phase of the inflammatory response by measuring changes in leukocyte velocity is extremely important. Currently available methods of quantifying these velocities in vivo, however, are labor intensive. For example, in a manual method of measuring leukocyte velocity or adhesion, videotape replay with a frame by frame analysis is used to count, or determine the velocity of individual leukocytes in a particular section of a blood vessel. This method of data collection is time consuming and laborious and restricts data collection to less than a minute for a single segment of each single vessel, and at only a few time points during the course of any extended test. Furthermore, this manual method and those utilizing computer-assisted systems have the ability of measuring leukocyte velocities in only a small section of one blood vessel at only a few time points per test.

In addition, because computer-assisted and manual methods are time-consuming and subjective in the choice of leukocytes, many leukocytes are often missed. In addition, this, by itself, makes the prior art methods inadequate for correlating, for example, adhesion protein expression sites within the wall of a particular blood vessel with leukocyte velocity.

This is also true for other systems of particles and objects. Similarly important is the quantification of traffic patterns by tracking changes in vehicular velocities. Because current methods are generally performed by off-line analysis of videotape, it is difficult to know during the time lapse on an on-going test how it is progressing.

Commercially available general-purpose image analysis software packages, such as Optimas BioScan, ImagePro Plus, and Inspector, have scripting or macro capabilities and therefore have some automatic analysis capability. These programs, however, require human intervention and decision making at multiple points in the analysis and cannot implement advanced analysis processes. Moreover, existing software is not fast enough for near real-time measurements of the velocities of particles such as leukocytes. Some of the commercial systems are used to assess leukocyte-endothelial interactions in vitro, where flow parameters of the fluid surrounding the leukocytes may be carefully controlled and monitored. Systems designed to work under these conditions do not work well in real time (in vivo) because of the visual heterogeneity in the tissue.

Over the past decade, several computer systems have been developed to assist with the measurement of rolling leukocyte velocities in vivo. While these systems are somewhat helpful, they utilize playback of a videotaped experiment, require the user to interactively select the white blood cells to be measured in sequential video frames, and record data from only a few minutes per test.

Recently, Sato et al. disclosed a technique for automatically tracking individual leukocytes in image sequences.

See, Sato Y., et al., "Automatic Extraction and Measurement of Leukocyte Motion in Microvessels Using Spatiotemporal Image Analysis", IEEE Trans. Biomed Eng. 44(4): 225–236 (1997). The Sato et al. method consists of a long series of computationally expensive steps and requires several user specified parameters. It does not appear that the system has feasible capability of real-time or near real time analysis.

Accordingly, it would be desirable to provide a system for the rapid, accurate and automatic measurement of tracking the velocities of particles, such as leukocyte rolling velocities and motor vehicles, in circulating velocities in real time. It also would be desirable that the system identify particle stoppages, e.g. adhering leukocytes, in multiple venues, e.g. vessels, and determine the period of time during which each stopped particle and object, e.g. adhering leukocyte, has zero or near zero velocity.

SUMMARY OF THE INVENTION

This invention, thus, relates to a method of tracking particles, generally comprising the generation of a time-varying sequence of images of a circulating venue containing a flow of particles, determining spatio-temporal intensity gradients within each of the images of the circulating venues, and identifying particles within the images of the circulating venue based upon the thus determined spatio-temporal intensity gradients. The particles or objects, e.g. leukocytes, within the images are matched with the corresponding identical particles, e.g. leukocytes, from other images using a heuristic technique. The method may additionally comprise other steps and/or execute some of the described steps in several stages. For purposes of clarity, the present invention will be generally described for the tracking of leukocytes and the determination of leukocyte rolling velocities. However, the present technology is applicable to any system of particles which circulate in one direction, such as street vehicular traffic, and the like.

For example, one preferred embodiment of the method of the invention comprises generating a time-varying sequence of images of a blood vessel containing a flow of blood, determining spatio-temporal gradients within each of the images of the blood vessel, identifying leukocytes within the images of the blood vessel based upon the spatio-temporal gradients, matching leukocytes within the images with the corresponding identical leukocytes from other images, determining an amount of translation of the matched leukocytes from one image to another, and determining movement characteristics of the leukocytes based upon the amount of translation.

In an exemplary embodiment, the time-varying image of a circulating venue containing a flow of particles or objects is generated by imaging the circulating venue using a video camera, selecting a rectangular area of interest within the image representative of a portion of the blood vessel, and then capturing sequential images of the blood vessel using a digital frame grabber. The spatio-temporal intensity gradients within each of the images of the blood vessel may be generated by subtracting an image from a previous image and applying a convolution mask to the resulting subtracted image to determine spatio-temporal derivatives. The spatio-temporal gradients may also be generated by convolving the image sequence with a 3D Sobel operator and representing the result as a 4-D data set, determining embedding angles for the 4-D data set, and determining spatio-temporal derivatives based upon the embedding angles. The leukocytes are then identified within the images by comparing the images to predetermined thresholds. The leukocytes may also be identified by performing a multifeature texture-based segmentation on the spatio-temporal gradients or by applying a multi-layer feed-forward neural network segmentation on the spatio-temporal gradients. The leukocytes may then be matched with corresponding identical leukocytes from other images by using a heuristic segmentation equation or, alternatively, a multi-layer feed-forward neural network segmentation or a correlation operator. The amount of translation of the matched leukocytes from one image to another may be determined, for instance, by calculating a center of gravity for each leukocyte and then calculating a Euclidean translation distance between the centers of gravity of the same leukocyte as it appears in separate images. The leukocyte velocity may be computed by dividing the translation distance by the time differential between the frames. The first five statistical moments of frequency distribution of the velocity may also be determined and used to characterize the immunological state of the organism. It has unexpectedly been found that the first three moments of frequency distribution of the velocity are sufficient to determine a useful approximation.

This invention also relates to an apparatus for practicing the above described method. The apparatus of this invention is capable of automatically tracking particle flow in real time, and comprises a video source providing a time-varying image of a circulating venue containing a flow of particles; an image capture unit capturing a sequence of images of the time-varying image; a processor identifying and tracking particles within the sequence of images of the circulating venue, said processor including one or more of a neural network processor, a heuristic processor, and a template-based correlation matching processor for tracking the particle.

The invention having now been generally described, other embodiments and objects relating to its functioning will now be described in experimental terms with reference to the accompanying drawings. It is well known to those skilled in the art that variations in this invention may be readily made. Therefore, such variations are considered to be within the scope and spirit of this invention.

BRIEF DESCRIPTION OF THE DRAWINGS

FIGS. 4A–4D illustrate the segmentation method of FIG. 3.

The invention will now be described in general in conceptual and experimental terms, with reference to preferred embodiments and to specific examples. Specific objects, advantages and features of the present invention will become apparent to those skilled in the art from the description that follows.

DETAILED DESCRIPTION OF PREFERRED EMBODIMENTS

This invention arose from the desire by the inventors to improve on prior technology for the measurement of leukocyte velocity in multiple vessels, particularly in the case of the early stages of the inflammatory response. One of their major goals in developing this technology was to provide a means for accurate and timely assessment, and subsequent control of leukocyte function. The inventors found that the currently available technology in this area was highly inadequate because it is labor intensive, time consuming, and only suitable for tracking a small fraction of leukocytes. These drawbacks severely limit the volume of data that may be obtained by existing methods.

Yet, the inventors were aware that leukocyte activation may be, by itself, the most damaging and deleterious aspect of a plurality of diseases because of the damage and/or destruction it may produce in otherwise normal tissues. This prompted them to pursue novel avenues in the search for a more effective method and apparatus for identifying and locating moving leukocytes appearing in one or more chosen venules, tracking multiple leukocytes simultaneously through sequential visible light video microscopic images, and providing rolling velocity data that is statistically indistinguishable from manually collected data, and give regional velocity profiles along the vessel wall.

The inventors designed an in vivo method and system that provides rapid, accurate, and automatic measurements of leukocyte rolling velocities. The method and system of the present invention, furthermore, is capable of identifying adhering leukocytes and determining the period of time during which each adhering leukocyte has zero velocity, as simultaneously acquired in multiple vessels. The present method and system permit the collection of a significantly increased volume of data from a single test, enable the identification of leukocyte adhesion sites, and provide greater accuracy of leukocyte activation indices. The present technology does all this while substantially reducing the analysis time.

Various exemplary embodiments of the invention will now be described with reference to the figures. These embodiments merely illustrate various aspects of the invention and should not be construed as limiting the scope of the invention.

Figure 1:
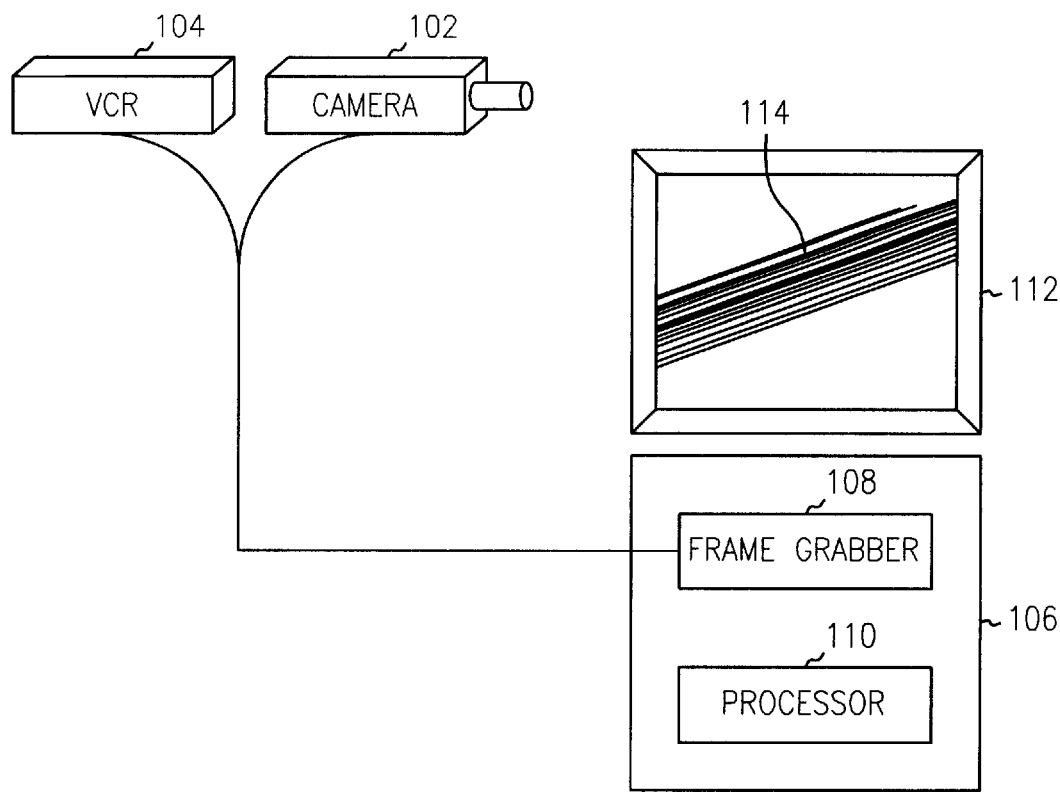
FIG. 1 is a block diagram illustrating a system for tracking leukocytes in vivo [computer] in accordance with an exemplary embodiment of the invention.

Referring to FIG. 1, a system 100 for automatically tracking the movement of leukocytes consists of a camera 102 to record images of in vivo microcirculation or a video cassette recorder 104 to play back previously recorded images of in vivo microcirculation and a computer 106 for processing the images. The computer includes a frame grabber 108 for digitizing the images of microcirculation and a microprocessor 110 or other circuitry for processing the digitized images. The computer may also include a display 112 for displaying the images.

Software provided on computer 106 is designed to automatically measure the velocity of rolling leukocytes in a sequence of microcirculation images captured by frame grabber 108. Alternatively, the software automatically measures the adherence duration of adhering leukocytes in the sequence of microcirculation images. In either case, the only user input required for the system to function is a designation of one or more areas of interest (AOI) 114. If none is provided, a default AOI may be used. Once the user has chosen an AOI, the software automatically tracks the leukocytes to determine, for example, the frequency distribution of the rolling leukocyte velocities within the AOI and associated statistical properties, the processing speed of the system is sufficient to provide real-time or near real-time tracking and analysis of the images.

The system tracks leukocyte movement based upon motion detected in the microcirculation images. Motion (real or apparent) in a digital image is known as optical flow. Motion estimation is the determination of optical flow vectors or the magnitude and direction of the optical flow in time. In general, an image is formed from the product of the reflective properties of the object surfaces and the illumination of the lighting scene.

Figure 2:
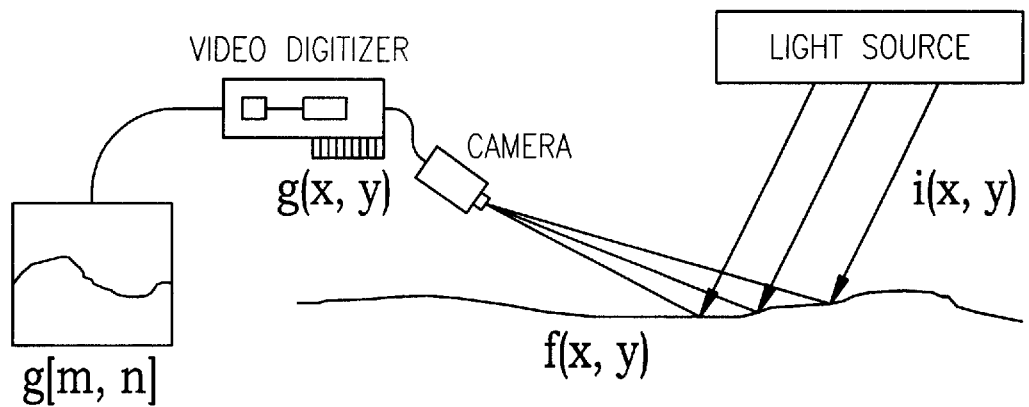
FIG. 2 illustrates the formation of a digital image for processing by the system of FIG. 1.

FIG. 2 illustrates the formation of a digital image. Here it should be noted that g(x,y) is a continuous function which is generally discretely sampled to produce the digital image g[m,n]. When discretely sampled in two dimensions, the illumination provides the pixel intensity data for a digital image $$g(x,y)=f(x,y)?i(x,y) \qquad (1)$$

wherein i(x,y) is the illumination function for the scene, f(x,y) is the reflectivity of the component objects and surfaces in the image, g(x,y) is the continuous image intensity data, and g[m,n] is the digital image. See, FIG. 1. To obtain a digital image from a continuous stream of images, the image function is generally temporally sampled at a frequency above the Nyquist limit of the intensity changes. Optical flow vectors then represent the change in image data with respect to time (dg/dt). The temporal variation in pixel intensity may be caused by dynamic changes in a) illumination function,
b) position of the camera,
c) position of the image objects,
d) the reflectivity of the image objects, or
e) any combination of these factors.

For in vivo microscopy of the microcirculation, however, most sources of dynamic change are fixed and major changes that occur in the digital image are caused by spatial changes (rotation, translation, scaling, or warping) of the image objects.

To restrict the amount of image data to be processed, one or more rectangular areas of interest (AOI) within an area may be selected by the user and digitized by the frame grabber. The digitized images generally are registered to ensure that the program compensates for any inter-frame translation of the field that has occurred. The system then locates the pixels that represent all moving objects within the AOI, and separates (segments) these pixels from the rest. Locating the largest spatio-temporal intensity gradients produces an image in which the segmented pixels form "blobs" that have shown a significant amount of change in gray level intensity from frame to frame and represent moving blood cells. The segmented pixels correspond to the red blood cells and the rolling leukocytes. These blobs are further classified by shape. The fast moving erythrocytes produce blobs that are thin and elongated "streaks", whereas the slower moving leukocytes produce blobs that are much "rounder" and larger. The spatio-temporal intensity gradient images contain two blobs for each corresponding leukocyte. A blob matching process uses the sum of the differences of the shape and size characteristics of the blobs and the spatial differentials in the transaxial (y) direction as a measure of the likelihood the blobs are from the same leukocyte. Once the pairs have been established, the centers of gravity are located for each blob, and the Euclidean distance between them measured.

In one particular embodiment, the frame grabber is the Matrox Genesis Frame Grabber which includes a TMS320C80 Digital Signal Processing (DSP) chip (Texas Instruments), with 16 MB image memory, and 8 MB video memory. The computer includes a 450 MHz Pentium II processor, with 128 MB of RAM and a 10 GB hard drive, and the system software running on the computer is written in the C programming language. The display is a 16 inch multisync monitor (e.g. Mitsubishi). Numerous other combinations of system components, however, may alternatively be employed. In specific instances, it may be desirable to incorporate a more powerful microprocessor to achieve real time or near real time processing.

Figure 3:
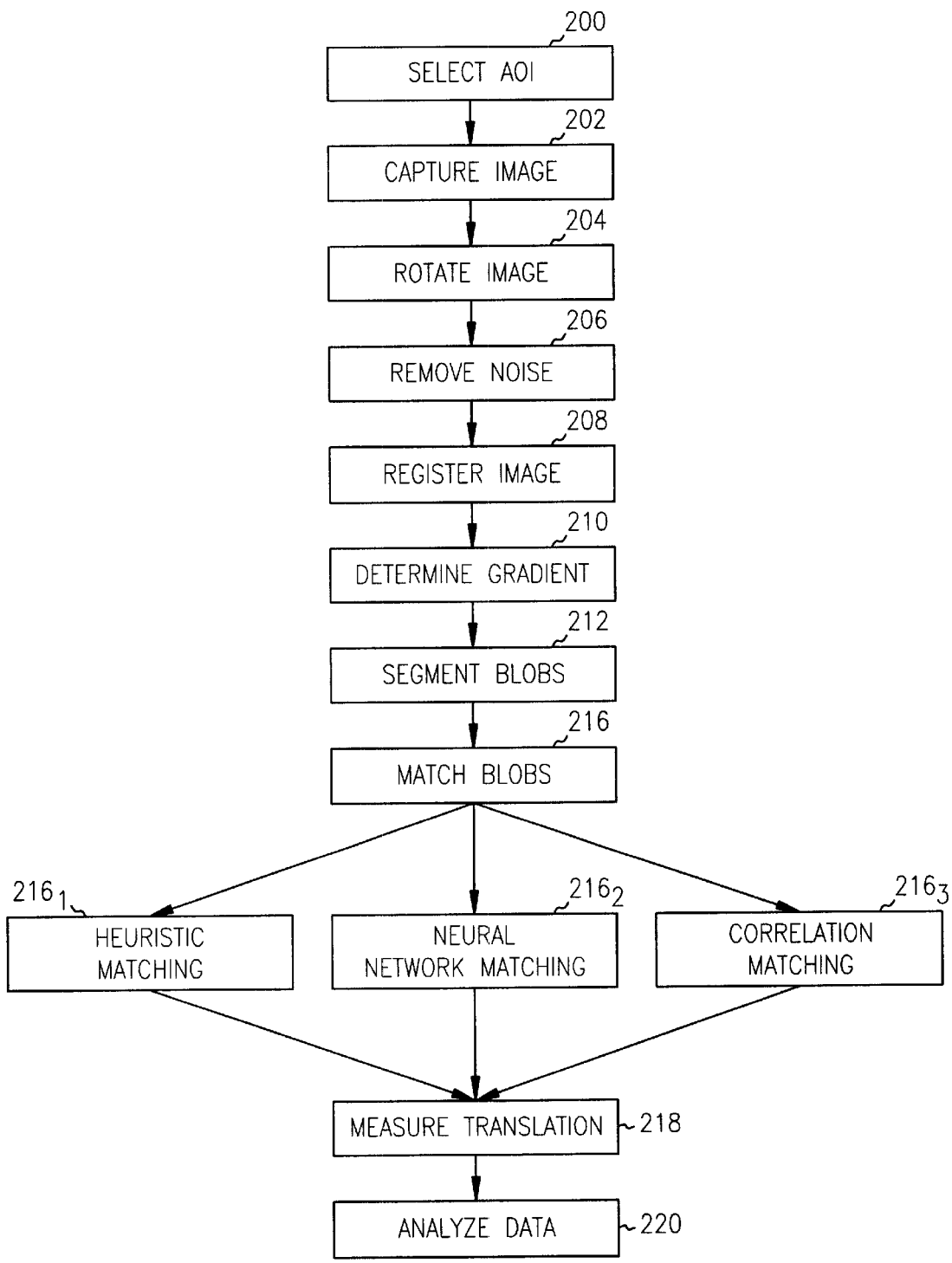
FIG. 3 illustrates a method for tracking rolling leukocytes using the system of FIG. 1.

Referring now to FIG. 3, the steps employed to input and process microcirculation images to track rolling leukocytes will be described. The area of interest (AOI) is selected at step 200 by the user to define a rectangular region of a venule to be digitized to provide the data for analysis. The AOI should encompass the entire inside of a venule, while excluding as much of the extravascular tissue as possible. AOI selection is initiated by positioning a graphic display of a box on the screen overlaying the image. The box size and orientation is changeable by the use of the computer mouse (not shown) or other input device. An arrow is also displayed within the box to indicate the direction of blood flow within the venule. From this information, the position, direction, and angle of image data are determined.

Once the AOI has been selected, a time-varying sequence of images with the AOI are captured at step 202. The frame grabber converts the analog video signal from either a camera or videotape into a digital representation of the individual intensities present in the scene. This digital information is stored in one or more pixel arrays. An analysis of the motion of the white blood cells in sample images has shown a maximum translation detected of about 340 pixels/sec. At this velocity and allowable translation distances, the maximum sampling rate is therefore preferably 3 Hz.

Image Rotation

If the AOI data array is orthogonal to the x and y axes, the processing of the data is easier and faster. Therefore the image is rotated at step 204, if needed, by the angle determined in step 200 to orthogonalize the image array. Since this angle is arbitrary, the position of the resulting data may not exactly match up with the previous pixel array. To compensate, a bi-linear interpolation is performed on the image data to determine the best intensity value for each pixel in the rotated image.

Noise Removal

At step 206, a filter is applied to the image to remove noise from the digital data. This noise may be already present in the video images, may be introduced by the frame grabber hardware, or may have been introduced by the rotation algorithm. Further processing to be described below employs high pass filtering of the image data and, hence, the initial low pass filter prevents the subsequent image from becoming too noisy to be analyzed.

The smoothing filter preferably operates in the spatial domain only. Temporal smoothing causes smearing of intensity gradient data. The first order differential operator is given by $$D_r=[-1\ 1] \quad (2),$$

which represents a causal filtering operation.

In other implementations, it may be desirable to apply a filter which smooths in both the spatial and temporal domains, such as 3×3 Gaussian low pass filter. Temporal derivatives are determined by use of a non-causal first order differential operator. This operator is given by the following convolution mask $$D_r = \frac{1}{2}[-1\ 0\ 1] \quad (3)$$

This operator is non-causal because it requires one frame of data before and after the point at which the derivative is calculated. However, in some cases, this filter is a good trade-off between speed of computation and approximation to the actual frequency response of the derivative function. Use of this operator means that the temporal gradient calculation will always occur one frame after the frame being analyzed. This produces is a small and consistent time lag.

For processing of images of large venules, an inverse filtering technique called deconvolution may alternatively be applied to the AOI data as described in Lim, J. S., Two-Dimensional Signal Processing, Prentice Hall, Englewood Cliffs, N.J. (1990). This technique sharpens the features in parts of the image that may be out of focus as a result of the large venule, but will also increase the processing time for the image.

Image Registration

During a time interval between individual frame captures, there is a possibility that the tissue may have moved by some amount in a possibly random direction thereby introducing an error in any translation measurements to be made. To remove random motion from the image sequence, each pair of successive frames is registered at step 208 to permit use of a common origin. To accomplish this, a 2-D cross-correlation is performed between two automatically determined sub-regions within each image. These regions are automatically chosen based on the coordinates of spatial gradients or edges that may be present in both the horizontal and vertical directions. The edges provide a strong signal that may be found in the area surrounding the same coordinates in the second frame. The amount of inter-frame translation is equivalent to the difference in the coordinates found in each frame for the same features. This translation vector is removed from the origin of the AOI in the second frame to register the two images.

Gradient Determination

At step 210 moving edges in the image sequence are detected. The leukocytes have moving spatial edges that produce temporal gradients detected by using image subtraction. To this end, the AOI of the first image is subtracted from that of the second image to yield a first order approximation of the temporal gradient for the interval. Any pixels that have not undergone a substantial change in intensity yield gradient values near zero. Hence, static features in the image are dark in the resulting gradient image. Note that derivative operations inherently pass high frequency (edge) information, and therefore are often sensitive to noise. Hence, additional filtering may be employed if needed.

More specifically, spatio-temporal intensity gradients are used to determine optical flow vectors under the assumption that the overall image intensity is conserved through time. This is modeled by equation 3. Given an image I(x,y,t) which is sampled from a sequence of images at time t $$I_x u + I_y v + I_t = 0 \quad (4)$$

wherein $I_x$ and $I_y$ are the partial derivatives of the intensity data in the spatial domain, It is the partial derivative in the temporal domain, and u and v represent the velocity vector components.

This implies that the illumination function is unchanging and the total image intensity over a short period of time is relatively constant. See, FIG. 1. In this scenario, moving image objects are delineated not only by spatial edges of the object boundaries, but also by the gradients produced by movement through the time domain. These spatio-temporal edges provide the signals used to locate the moving objects in a static background.

As an alternate approach in quantifying spatio-temporal gradients, a method described by Liou and Jain, wherein spatio-temporal image data from a sequence of images are analyzed as a spherical 4D data set. See, Liou S. H. and R. C. Jain, "Motion Detection in Spatio-Temporal Space", Comp. Vision, Graphics and Image Process, 45: 227–250 (1989). The angles of the gradients found in this spherical space yield not only the spatial and temporal gradient information, but also a confidence level in terms of what is referred to as an embedding angle. This angle accounts for the fact that motion information can only be accurately calculated in regions in which there is strong edge information present. The embedding angle gives a measure of how well the calculated movement vectors correspond to the actual ones in the image sequence.

Blob Segmentation

At step 212, segmentation is performed by separating pixels having a large temporal intensity gradient from other pixels. Segmentation is preferably performed by applying an empirically determined threshold value above which a pixel is considered to be part of an object of interest, e.g. leukocyte. Static or dynamic threshold methods may be employed, with or without prior contrast enhancement. The segmentation process yields an image of "blobs" of connected pixels that represent the location of the moving leukocyte.

Figure 4C:
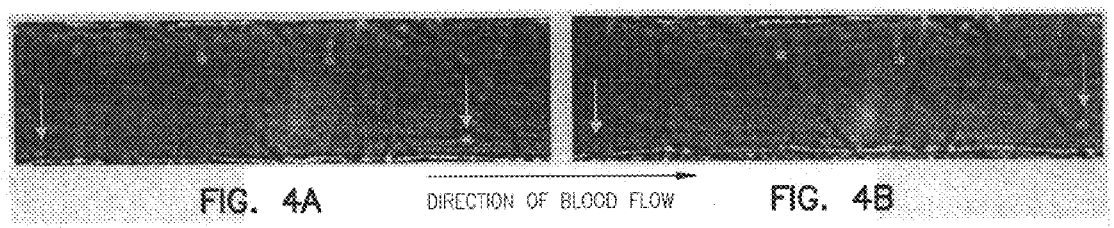
Figure 4D:
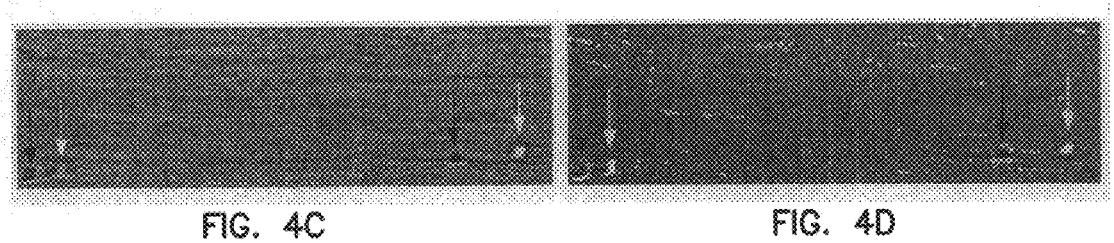

FIGS. 4A–4D illustrate the segmentation method of step 212. FIGS. 4A and 4B show the areas of interest (AOIs) of two successive frames of the transmitted light image. For these images, tissue movement was not evident and the background was spatially static. At video frame rates (30 Hz), the erythrocytes appear as parallel blurred streaks in the direction of flow. By subtracting the digital information in FIG. 4A from FIG. 4B, a difference image of FIG. 4C is formed. The difference image is then thresholded by two values yielding a three-level image FIG. 4D. In this image, the white pixels represent image points with significant gray level increase, the black pixels represent those that had a significant decrease in intensity, and the gray pixels are those that have no significant change. Post-processing is performed using a binary morphological opening filter to remove small noise blobs and to smooth out the perimeters of the larger blobs. Shape and size parameters are then used to classify the objects as either erythrocyte streams or rolling leukocytes (see next section). In this way, the entire field of rolling leukocytes is selected without human intervention. Note that the difference filter does not detect leukocytes that adhere to the vessel wall because these are interpreted as part of the background.

Alternatively, an automatic multi-feature texture based segmentation wherein two or more features from the image to determine the best classification of the constituent pixels. Examples of these features include the gray level intensity and intensity organizational (texture) metrics (e.g. local standard deviation). This method has a high likelihood of succeeding, since leukocytes generally have a higher intensity and different textures than the surrounding blood. Yet another approach is to use a multilayer feed-forward neural network to classify pixels within the AOI as belonging to a leukocyte or background.

Once blobs of significant intensity changes have been segmented from the rest of the image, images are compared at step 216 to match each blob location with its previous location in previous images. Preferably, a heuristic method 216 is employed wherein the position, shape, and size characteristics of blobs are compared with blobs in previous images. Similarity of blobs, as well as, known blood flow direction and magnitude are used to determine the most likely matching blob.

More specifically, the heuristic blob matching method of step 216 uses the difference between the y (axial direction) coordinates for the two blobs, the difference in their areas, and the difference between their shapes as quantified by a compactness metric. The most compact object is a circle with compactness equal to one, and the compactness value rises as the object becomes less circular. Compactness C is a measure of the "roundness" of a blob. It is calculated by the following equation $$C = \frac{P^2}{4\pi A} \quad (5)$$

wherein

P is the perimeter of the blob, and

A is the area.

A circle has the lowest possible compactness C=1), and the value rises as the object becomes less circular. A matching blob is chosen that minimizes the sum of these factors, and also meets an empirically determined allowable translation criteria. The maximum allowable y direction translation may be, for example, nine pixels (absolute value). The maximum allowable x direction translation may be, for example, 128 pixels with a positive x direction translation. These values are empirically determined. For example, if the maximum leukocyte velocity actually measured is 96 pixels in one-half second, then the maximum permissible velocity is preferably set to a value somewhat greater than that value, e.g. 128 pixels per one-half second.

The process of process of step $216_1$ may best be illustrated with reference again to FIGS. 3-A–3D. The aforementioned characteristics (difference between the y coordinates, difference in area, and difference in compactness) are determined between each white blob and every black blob. From empirically determined rolling paths, maximum allowable translation distances for each direction are computed. For a given white blob to match up with a certain black one, the y differential (transaxial movement) had to be a value near zero. The difference between the values of these three features from each possible blob pair are used in the heuristic equation to compute similarity to best choose which pair of blobs should be matched.

Alternatively, a multilayer feed-forward neural network is employed at step $216_2$ using the same blob features, but as input values to a multi-layer feedback neural network. The network is initially trained on a set of 100 images of microcirculation previously analyzed by hand for the leukocyte velocities. Using this data as a training set, the network is trained to recognize blob pairs based on the given features from the training set. In other words, the network is trained on the image data to correctly match up the corresponding black and white blobs. Network weights are updated using an error back propagation technique for continuous bipolar perceptrons described by Zurada. See, Zurada, J. M., Introduction to Artificial Neural Systems, West Publishing, St. Paul, Minn. (1992). Four nodes may be employed in a hidden layer with a learning constant of c=0.05. Appropriate weight values are given by the following for the output layer weights $$w'_{kj} \leftarrow w_{kj} + c\delta_{ok}y_i \quad (6),$$

and for the hidden layer weights $$v'_{ji} \leftarrow v_{ji} + c\delta_{yj}z_i,$$

wherein w represents the output layer weights, v represents the hidden layer weights, c represents the learning constant, dok represents the error term for the output layer, dyj represents the error term for the hidden layer, y is the hidden layer output, and z is the input data.

In yet another alternative technique, cross-correlation is employed $216_3$ to find the position of a blob in the subsequent frame. Correlation is less susceptible to lighting changes and obstructions than other matching techniques, but typically only works over a short time period because of morphological changes in the leukocytes that may occur over a longer time. By correlating the intensity information present in the region with a target area in a subsequent image, the path of the region over the elapsed time may be determined. The correlation method of motion estimation uses template matching to locate features present within the image. The correlation of the two regions is derived from equation 2, which is based on Pearson's correlation coefficient r Î[−1,1]

$$r = \frac{\sum_i (x_i - \bar{x})(y_i - \bar{y})}{\sqrt{\sum_i (x_i - \bar{x})^2} \sqrt{\sum_i (y_i - \bar{y})^2}} \quad (7)$$

In this equation xi and yi are the components of regions X and Y, and are the means of the two regions being correlated. This feature-based technique assumes the location of the intensity information is changing faster than the organization of the information. Therefore, the organization of a region of the image would have little or no difference from one image to another over a small time differential.

When two cells are in close proximity, the feature method may choose an incorrect translation vector. Accordingly, a directional probability factor may be calculated and incorporated along with previous vector information into the correlation equation. Also, a probabilistic relaxation scheme may be employed in which regions with similar flow vectors reinforce each other, and dissimilar ones suppress each other as described by Rosenreid et al.(1976) and Wu (1975). See, Rosenfeld A., et al., "Scene labeling by relaxation operations", IEEE Trans. Syst. Man and Cybern. SMC-6(6): 420433 (1976) and Wu Q. X., "A Correlation-Relaxation-Labeling Framework for Computing Optical Flow-Template Matching From a New Perspective", IEEE Trans. on Pattern Analysis and Machine Intel., PALMI 17(9): 843–853 (1995).

Translation Measurement

At step 218, translation of the matching blobs is determined by computing the Euclidean distance between each pair of matching blobs. This is performed by calculating the vector between the blobs then subtracting the inter-frame translation vector previously determined by the registration process to obtain the true amount of translation of the cell. The actual velocity is this vector divided by the time differential between the frames used to find the blobs. Speed of the leukocyte can also be determined by taking the magnitude of the velocity vector.

The histogram of the frequency distribution of the translations is calculated after a first set of translation measurements are obtained and the distribution is displayed on the video monitor. The frequency distribution is updated for each successive image and redisplayed.

At step 220, the first five statistical moments of the frequency distribution are then calculated to characterize the histogram. Alternatively, the first three moments may be used to give values that quantitatively characterize the frequency and distribution and allow for useful statistical comparisons. The moments of this histogram (mean, variance, skewness, and kurtosis) yield quantitative measures of current leukocyte activity. The first moment (mean) is the location of the geometric center of the distribution, the second central moment (variance) describes the amount of spread of the data around the mean, the third central moment (skewness) describes the symmetry of the distribution, and the fourth central moment (kurtosis), the flatness of the histogram. The central moments are centered on zero to remove the mean value from the calculations.

Changes in these values are indicative of changes in the physiological state of the leukocyte and endothelial components of the immunological system of the organism being studied. The Chi-square test is used to give a statistical assessment of the quality of the automatically collected data compared with that of three independent human observers for the same set of images.

Also in step 220, a map of the mean velocities in each region of the AOI is generated. This analysis provides a numerical description of spatial variations of adherence activity that may occur along the vessel wall. These differences are typically due to the differential expression of adhesion molecules at the endothelial surfaces. The effect of changes in the immunological system or in an inflammatory process are then correlated directly with changes in rolling and sticking behavior, and the location of those changes in the microcirculation.

In addition to the mean and variance of leukocyte velocity, the system may also calculate at step 220, the leukocyte "equivalent flux", or the equivalent number of cells moving across the field of view in a given amount of time. Equivalent flux (FE) is computed by tracking each leukocyte movement as an independent event. By doing so, the percentage of the field of view that has been traversed in a certain time interval is determined. The sum of all of these percentages yields the equivalent flux. Note, though, that if the individual velocities are not analyzed independently, then the frequency distribution becomes strongly biased toward the slower cells since they are in view for more frames than the faster ones. Therefore, a single cell moving slowly can produce more values in the frequency distribution than a fast moving cell. Equivalent flux obviates this problem by computing the overall flux of the field of view, while still taking into account rapid changes in the leukocyte behavior. The equation for computing equivalent flux FE is given by $$F_E = \frac{1}{l} \sum_{x=1}^{V_{Max}} x f(x), \quad (8)$$

wherein 1 is the length of the AOI in the direction of flow, x is the given velocity, Vmax is the maximum allowable velocity, and f(x) is the frequency of velocity x.

Three moments—number of individual translations measured, mean translation for cells, and the variance of the measured translations—give values that quantitatively characterize the frequency distribution and allow for statistical comparisons between distributions. This measurement is termed the equivalent velocity.

Thus, various aspects of the invention have been described with respect to FIG. 3. Each block illustrated within FIG. 3 represents either a method step or an apparatus element for performing the corresponding method step. The apparatus elements are also referred to herein as processors, units, and the like. The apparatus elements may be implemented using any technology appropriate for the function being performed, such as application specific integrated circuits (ASIC's) or generally programmable microprocessors. For apparatus elements implemented using a programmable microprocessor, the apparatus element may also include software stored within a memory device coupled to the microprocessor.

EXAMPLES

A set of 100 test images of mouse cremaster muscle microcirculation was collected over a 50 second time period. The images were analyzed manually to provide test data for comparison with the automatically collected data. The method required a minimum translation distance of about half the diameter of the leukocytes (10 pixels) which yields a minimum detectable velocity of 15 pixels/sec.

Figure 5A:
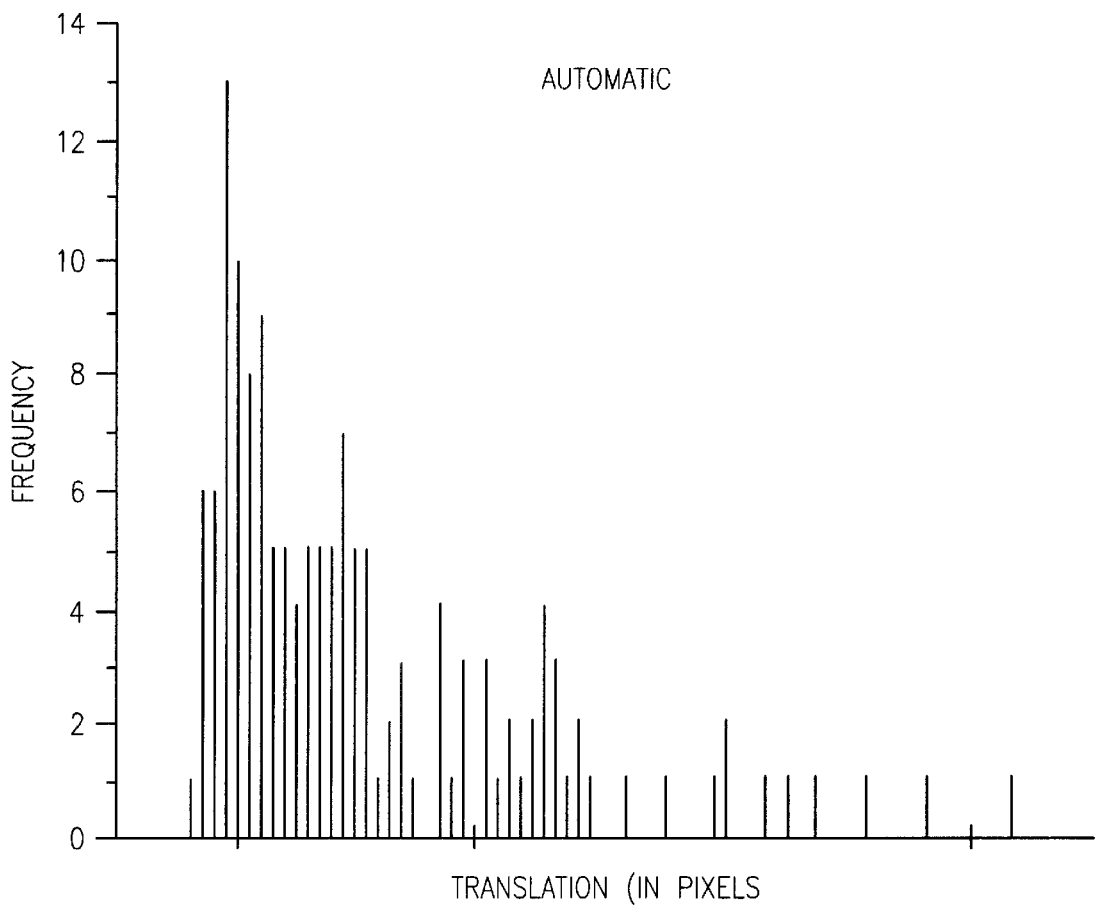
FIGS. 5A–5B illustrate a comparison of velocity distribution measurements generated automatically using the method of FIG. 3 and other measurements taken manually.
Figure 5B:
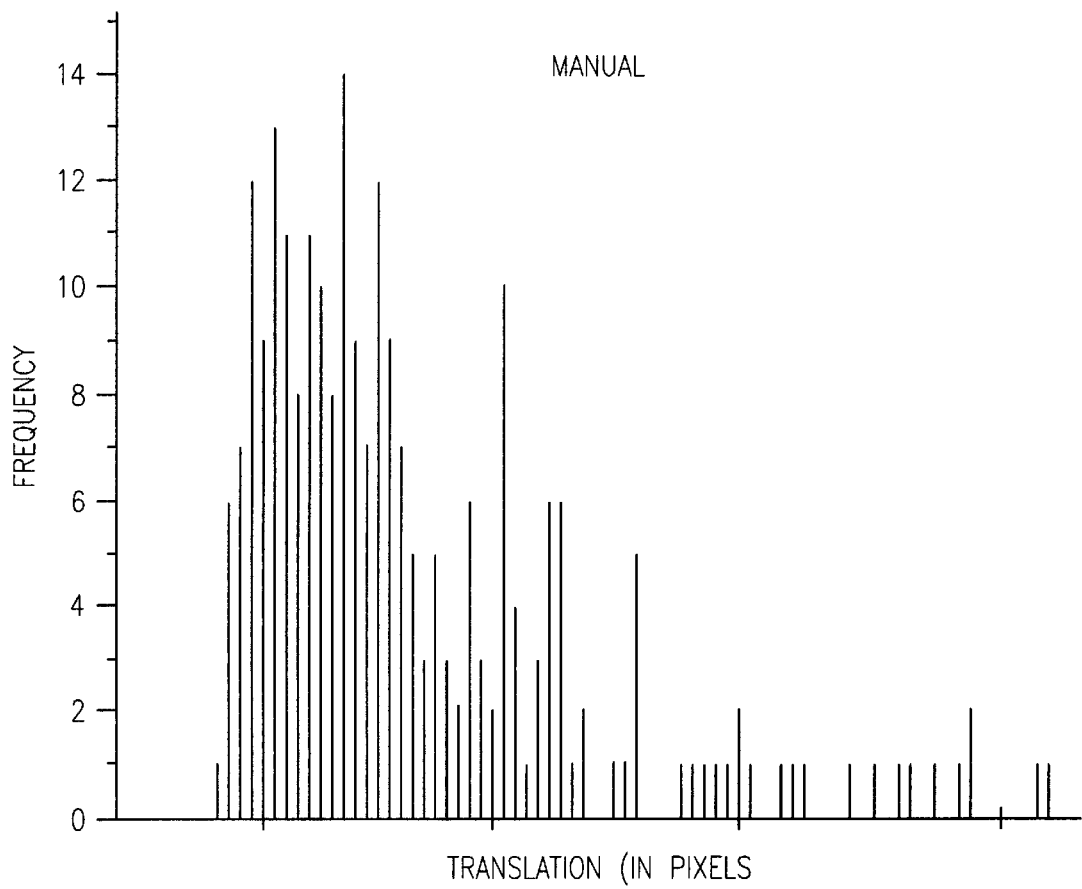

FIG. 5A shows manually collected leukocyte velocity frequency distribution and FIG. 5B shows automatically collected distribution. These data were collected by the artificial intelligence or heuristic blob matching method. xP2 test was applied to the frequency distributions to determine the "goodness of fit" between them. The resulting value had a probability less than 0.10 that the distributions are sampled from different populations. A Student's t test was also run on the means. The test had a t value=0.223, with the degrees of freedom value [<]=354, for a probability of less than 0.1% that the two means are statistically different.

Leukocyte activation resulting in adherence, e.g. rolling and/or sticking, of the cell to the vascular wall and subsequent infiltration into the tissue, has been observed to occur in many clinical conditions. Among the most common conditions are the basic inflammatory reaction, immune and auto-immune diseases, arthritis, vascular leak syndrome, burns, organ rejection, and shock, among others. It is postulated that this process is crucial to the role of the leukocyte in protecting the body against foreign organisms and substances. Moreover, it is widely believed that uncontrolled leukocyte activation may, in itself, be the most damaging and deleterious aspect of a disease because normal tissue may be damaged or destroyed. Thus, the present technology clearly advances the diagnostic field by providing a means for the continuous measurement of leukocyte velocity in multiple vessels. This capability is of particular importance for application during the early stages of an inflammatory response, which is essential to assessing and controlling (modifying) leukocyte function. As already pointed out, current methodology in this area is time consuming and severely limits the quantity of data that can be collected.

The present method may be reduced to practice by means of the apparatus for automatically tracking particle or object flow in real time provided by the inventors. The apparatus in its simplest embodiment, comprises a video source providing a time-varying image of a circulating venue containing a flow of particles or objects; an image capture unit capturing a sequence of images of the time-varying image; and a processor identifying and tracking particles or objects within the sequence of images of the circulating venue, said processor including one or more of a neural network processor, a heuristic processor, and a template-based correlation matching processor for tracking the particle or object.

In one embodiment, this invention also provides an apparatus where the processor comprises a spatio-temporal intensity gradient detection unit detecting spatio-temporal intensity gradients within the sequence of images of the circulating venue, a segmentation unit detecting particles or within the sequence of images of the circulating venue based upon the spatio-temporal intensity gradients, a particle or object matching unit matching particle or object within the sequence of images with the corresponding identical particle or object from other images, said processor including one or more of a neural network processing unit, a heuristic processing unit, and a template-based correlation matching processing unit, a translation determination unit determining an amount of translation of the matched particle or object from one image to another, and a movement characteristics analysis unit determining movement characteristics of the particle or object based upon the particle translation distance. The video source may be a VCR, or a video camera. In one embodiment, the image capture unit is a frame grabber. In another embodiment, the spatio-temporal gradient detection unit subtracts one image of the sequence of images from a successive image. When suitable for a specific application, the segmentation unit is made to compare the spatio-temporal gradients of the images to predetermined threshold values representative of particle characteristics. Another preferred feature that may be added is that wherein the translation determination unit determines the velocity of matched particle from one image to another, preferably wherein movement characteristics analysis unit determines a frequency distribution of the velocities of particle or object, more preferably wherein the movement characteristics analysis unit also determines the first five moments of the frequency distribution of the velocities of particle or object.

The apparatus of this invention may be applied to tracking particles such as leukocytes, where the circulating venue is a blood vessel, and the apparatus tracks the rolling flow of leukocytes. In another application, the present apparatus may be applied to particles such as vehicles or animals, including human and nonhuman animals, where the circulating venue is a vehicular or animal circulation venue. The vehicles being tracked may be manually operated and motor ground vehicles, and the venue may be streets. However, the vehicles may also be airborne vehicles, in which case the venue is an air vehicular path, or water borne vehicles, where the venue is a water vehicular path.

The present invention, thus, is applicable not only to tracking particle flow, e.g. leukocytes, and vehicular flow and rolling velocity but, in addition, in the case of cells to the diagnosis of diseases and conditions associated with alterations in leukocyte rolling velocity and "sticking". Examples are inflammatory diseases, immune and auto-immune diseases such as inflammatory bowel disease (IBD), Crohn's disease (CD), Systemic Lupus Erythematosus, diabetes mellitus, arthritis, vascular leaks such as in vascular leak syndrome, burns, tissue and organ transplants (rejection), skin grafts, local infection, cytokine treatments, tissue trauma, systemic infections, reperfusion injury, dental procedures, local and systemic inflammation, and shock, among others.

This invention, thus, provides a technology for tracking particles such as leukocytes in real time, and without human error and bias. When analyzing a laboratory experiment, the changes in the leukocyte behavior are reflected in changes in the frequency distribution and the resulting changes in the statistical moments. When the system is first implemented, and perhaps from time to time thereafter, the automatically collected histogram is preferably compared with the manually collected histogram of the same data to verify that the automatically collected data is statistically indistinguishable from the manually collected data. If not, the various empirical parameters mentioned above are adjusted as needed.

Alternative Methods

The aforementioned method relates to the tracking of the velocity of rolling leukocytes. Additionally, the position and sticking duration of firmly adherent leukocytes can be detected using similar techniques. This requires a different approach since pixels representing stationary leukocytes have no intensity gradients in the temporal domain. Accordingly, a texture-based segmentation procedure is employed which combines the features of pixel intensity and local intensity organization (texture analysis), and then classifies pixels as being part of a leukocyte or not. Stationary segmented cells have translation distances near zero. The gray level data from the pixels in the stationary cells, as well as their spatial organization will be used as features directly in an automatic entropic segmentation technique or as input values to a multilayer feed-forward neural network. A temporal low-pass filter, such as thresholding temporal variance, may be employed as a pre-processing step. This method works because the stationary cells have less variation in their intensities over a period of time than areas within the blood stream with moving cells.

Depending upon the implementation, the present technology for tracking particles has a number of advantages over previous manual or computer assisted methods including, although not exclusively, the following.

1. The method and system are automated with minimal human interaction, which decreases human bias and error.

2. When implemented to detect leukocyte adhesion, this method and system locates leukocyte adhesion sites throughout the wall of the same blood vessel and, thus, helps identify sites of adhesion molecule expression.

3. The method and system of the invention assesses multiple blood vessel responses to a given inflammatory stimulus rather than that of a single segment of a single venule.

4. The system can simultaneously determine the rolling velocities of particles in a circulating venue, e.g. leukocytes in a blood vessel, the number of stopped particles and objects, e.g. firmly adherent leukocytes, and the duration of each particle's stay in a stationary position.

5. The system processes data in real time or near real-time. Hence, test results may be analyzed on-line, which eliminates time consuming post-test processing of videotapes.

6. In the case of fragile cells the invention may utilize transmitted light images to avoid phototoxic effects that occur with the use of fluorescent markers attached to them.

7. The system may utilize fluorescent dyes to identify sub-populations of cells, e.g. leukocytes, or other markers for different types of particles and objects, and determine their individual velocity profiles.

With information provided by the techniques of the invention, adhesion protein expression can be correlated with leukocyte rolling and sticking measurements at distinct points of the vascular wall. Sub-populations of leukocytes (lymphocytes, neutrophils, and monocytes) and their velocities can be identified. Currently, the only way to differentiate between types of leukocytes is with fluorescence. With fluorescence, the cells typically have to be removed, labeled, and re-injected. If they are labeled in vivo, there is an increased chance of endothelial toxicity resulting from excess fluorochrome and light.

The relevant text of the specific references mentioned in this patent is incorporated herein by reference to the extent that it may contribute to the understanding of the present invention. Various embodiments of the in vivo method and system of this invention for tracking leukocytes have now been described. A wide range of other embodiments are possible within the four corners of the present invention as an artisan in the field would know. These different embodiments are consistent with the general principles of the invention and, therefore, the specific embodiments described above should not be construed as limiting the scope of the invention which is to be interpreted by the claims which follow.

We claim:

1. A real time method for tracking the flow of particles comprising:

generating a time-varying image of a circulating venue containing a flow of particles;

identifying at least one particle within the time-varying image of the circulating venue;

tracking the flow of such identified particle using a technique selected from a group consisting of a heuristic technique, a neural network technique, and a correlation technique using template matching.

2. The method of claim 1 wherein the particle is a leukocyte, the method is an in vivo method for tracking leukocyte flow and the circulating venue is a blood vessel.

3. The method of claim 1 wherein particles within the time-varying image are identified by determining spatio-temporal intensity gradients within a sequence of images of the circulating venue; and identifying particles within the sequence of images based upon the spatio-temporal gradients.

4. The method of claim 3 wherein the flow of particles is tracked by matching particles within the images of the sequence of images with the corresponding identical particle from other images within the sequence;

determining the distance of translation of the matched particle from one image to another; and determining movement characteristics of the particle based upon the particle translation distance.

5. The method of claim 3 wherein the sequence of images of the circulating venue containing a flow of particles is generated by imaging the circulating venue using a video camera;

selecting an area of interest within the video camera image representative of a portion of the circulating venue; and capturing images of the circulating venue within the area of interest using a digital frame grabber.

6. The method of claim 3 wherein the spatio-temporal intensity gradients within each of the images of the circulating venue is determined by convolving the spatio-temporal intensity data with a three dimensional Sobel mask;

representing the result as a 4-D data set;

determining embedding angles; and determining spatio-temporal derivatives based upon the embedding angles.

7. The method of claim 1 wherein the particle within the image of the circulating venue is identified by applying a multi-layer feed-forward neural network segmentation on an intensity value of constituent pixels of the image.

8. The method of claim 1 wherein the particle within the images is matched with the corresponding identical particles from other images wherein a heuristic matching equation is applied by selecting first and second images;

determining the shape and size of each particle in the selected images;

determining the vertical translation distances between each particle of the first image and each particle of the second image;

inputting maximum expected horizontal translation and vertical translation distances for each particle;

applying the shape, size and vertical translation distances to match the particle of the first image with the corresponding identical particle of the second image.

9. A method of identifying leukocyte adhesion sites, comprising conducting the method of claim 2 and assessing whether there is a decrease in the leukocyte rolling velocity when compared to the velocity of the identical leukocyte in the previous images.

10. A method of determining a degree of leukocyte activation, comprising conducting the method of claim 2 and correlating the movement characteristics of leukocytes and their degree of activation as compared to a control leukocyte that is known to be non-activated.

11. A method of diagnosing a condition associated with altered leukocyte rolling velocity and/or adhesion comprising conducting the method of claim 2 in a subject suspected of having such condition and comparing the results of the method to the leukocyte rolling velocity and/or adhesion of subjects known to have the condition and of subjects known to be free of the condition.

12. An apparatus for automatically tracking particle flow in real time comprising:

a video source providing a time-varying image of a circulating venue containing a flow of particles;

an image capture unit capturing a sequence of images of the time-varying image; and a processor identifying and tracking the particle within the sequence of images of the circulating venue, dais processor including one or more of a neural network processor, a heuristic processor and a template-based correlation matching processor for tracking the particle.

* * * * *